United States Patent [19]

Soichet

[11] 4,312,884

[45] Jan. 26, 1982

[54] TREATMENT OF HERPES SIMPLEX

[76] Inventor: Samuel Soichet, 1088 Park Ave., New York, N.Y. 10028

[21] Appl. No.: 213,830

[22] Filed: Dec. 8, 1980

[51] Int. Cl.³ ............................................ A61K 31/35
[52] U.S. Cl. .................................................. 424/283
[58] Field of Search ........................................ 424/283

[56] References Cited
PUBLICATIONS

Chemical Abstracts 79:38883j (1973).
PDR, 27th Ed., 1973, pp. 1475 & 1476.

*Primary Examiner*—Jerome D. Goldberg
*Attorney, Agent, or Firm*—Ostrolenk, Faber, Gerb & Soffen

[57] ABSTRACT

Spectinomycin is used in the treatment of herpes simplex.

7 Claims, No Drawings

TREATMENT OF HERPES SIMPLEX

BACKGROUND OF THE INVENTION

Herpes simplex is an infection by herpes simplex virus which is marked by the eruption of one or more groups of vesicles on the vermillion border of the lips, at the external nares, or on the glans, prepuce, or vulva. The infection is commonly recrudescent and reappears during other febrile illness or even physiological states such as menstruation. The infection has also been called, according to its site, fever blisters, cold sores, herpes digitalis, herpes catarrhalis, herpes facialis, herpes febrilis, herpes genitalis, herpes labialis, herpes mentalis, herpes preputialis and herpes progenitalis.

Herpes simplex virus type 1 is known as the "skin" or the "above the umbilicus" virus and type 2 is known as the "genital" or "below the umbilicus" virus. The two types cannot be distinguished in a culture, but can be distinguished on the basis of the antibodies generated upon exposure to the virus. The two types cross react with one another in the laboratory so that they are considered "cousins".

Various treatments of herpes simplex have been proposed. Asculai, U.S. Pat. No. 4,147,803 teaches that certain sorbitan derivatives have anti-herpetic activity and DeLong, et al., U.S. Pat. No. 3,639,612 teaches such activity for certain chalcogen containing heterocyclic compounds. Stedman, U.S. Pat. No. 3,555,355 discloses that certain cycloalkylamines have activity against herpes simplex and Fleming et al., U.S. Pat. No. 3,829,578 teaches that certain bis-basic ethers and thioethers of xanthene and xanthen-9-ones have anti-viral activity.

It is the object of this invention to provide a new method of treating herpes simplex. This and other objects of the invention will become apparent from the following description thereof.

SUMMARY OF THE INVENTION

This invention relates to the treatment of herpes simplex and more particularly to the treatment of herpes simplex by the administration of spectinomycin.

BRIEF DESCRIPTION OF THE INVENTION

It has been found that spectinomycin is effective in combating herpes simplex infections. This antibiotic is also known as actinospectacin and espectinomicina and is chemically decahydro-4a,7,9-trihydroxy-2-methyl-6,8-bis(methyl-amino)4h-pyrano[2,3-b][1,4]benzodioxin-4-one. The dihydrochloride pentahydrate salt is commercially available in the United States under the trademarks Spectogard, Stanilo, Togamycin and Trobicin. Spectomycin is an aminocyclitol antibiotic produced by a species of soil microorganism and is active against most strains of *Neisseria gonorrhoeae.*

Spectinomycin hydrochloride pentahydrate is commercially available in 2 and 4 gram packages with an accompanying diluent which is bacteriostatic water for injection with 0.9% w/v benzyl alcohol. The vials are shaken vigorously after mixing and before withdrawing the dose. Administration is by intramuscular injections which should be made deep into the upper outer quadrant of the gluteal muscle. The recommended dosage for patients who are treated after failure of previous antibiotic for gonorrhea is an injection of 5 milliliters intramuscularly for a 2 gram dosage.

The following United States patents disclose spectomycin, its preparation and/or purification and antibiotic activity: U.S. Pat. Nos. 3,206,360; 3,234,092; 3,245,797; 3,269,907; 3,272,706; 3,318,867; 3,355,355; 3,804,858 and U.S. Pat. No. Re. 26,164.

It has been found that herpes simplex can be treated by administering spectinomycin in the same manner as the antibiotic has been used for the treatment of gonorrhea. Additionally, the antibiotic can be applied topically in the form of an ointment. It can also be applied in combination with other known antibiotics such as the tetracyclines, which may be particularly useful in the treatment of patients having Mycoplasma Hominis and/or Chlamydia Trachomatis in association with the herpes.

An anti-herpetic effective amount should be employed and this varies depending on the severity of the infection. In some instances, a 2 gram dosage may be adequate and in most instances a 4 gram administration may be indicated and, on occasion, additional administration of 2 to 4 grams may be desirable. It has been found that, generally, administration of 4 grams of spectinomycin dihydrochloride pentahydrate is sufficient. It should be appreciated that each patient with symptomatic herpes simplex describes a different routine of behavior of reaction to the instant treatment. Most register an arrest of the infection, if acute, or if during an attack or crisis. In general, the infection is arrested during the first 24 hours in the symptomatic cases and 95% "cured", i.e. disappearance of symptoms including lesions, in 72 hours. Some patients reveal that areas of redness around the eyes (considered conjunctivitis), the nostrils and other areas of itching and other parts of the skin disappear after treatment. It should be appreciated that the instant treatment is not a vaccine type of treatment in that it will not prevent recurrence of the infection and each reinfection will have to be re-treated. This fact is evident from cases which had received spectinomycin dihydrochloride pentahydrate prior to the existence of a herpes infection and such prior treatment did not prevent the herpes simplex infection from occurring.

Spectinomycin dihydrochloride pentahydrate sold under the trademark Trobicin has been used clinically to combat herpes simplex infections. A reveiw of some of these cases is as follows:

Case 1: This female patient had buccal herpes simplex for over 20 years. She was injected intramuscularly with 4 grams of the antibiotic whereafter the symptoms disappeared. A follow-up examination about two and one half years after the injection did not reveal the presence of any symptoms of the herpes infection.

Case 2: This patient had an infection in the vulva which recurred every three to four months over a period of three years. Administration of 2 grams of Trobicin was follows by an attack of 2 days duration instead of the usual 7 day period. Administration of an additional 2 grams of Trobicin was sufficient to cause disappearance of the symptoms for 16 months.

Case 3: This patient had been suffering with infections of the thighs and anus for 4 years. Administration of 4 grams caused the symptoms to disappear and follow-up examination about nine months later showed no recurrence.

Case 4: Administration of 4 grams caused the disappearance of symptoms in this patient who had severe herpes infections of the vulva and vagina for about 4 months.

Case 5: This patient had been suffering with infections in the vulva about every 3 months for about 4 years. Administration of 4 grams of the antibiotic caused all "scratchy" feelings to disappear.

Case 6: This patient had outbreaks of herpes simplex every 1-2 months in the roof of the mouth for about 4 years. Within 24 hours after administration of 4 grams, the ulcerations of the mouth roof were gone.

Case 7: This patient had herpes outbreaks for about 2 years in the vulva and vagina on a monthly basis coincident with menstruation. There was no recurrence of the infections during the six menstrual cycles following administration of a 4 gram dose of the antibiotic.

Case 8: This patient had severe herpes infection of the penis every 2 weeks for a period of about 6 months. After administration of 4 grams of Trobicin, the symptoms disappeared and did not recur during the next 6 months while the patient was being observed.

Of the first 38 patients who received the spectinomycin treatment, only one failed to respond to treatment while all other symptomatic patients have shown excellent results. Except for the first two cases mentioned above, the dosage used was 4 grams of the antibiotic administered as a 5 cc. (containing 2 grams active ingredient) injection on each buttock. Two patients received a second injection of 2 grams. One of these, a 16 year old with an acute vulvitis, was controlled in 17 hours and reported that she felt "different" within 5 hours after the injection. The other patient still felt one blister during her first menstrual period after the injection and reports that she has felt "cleaner" since the treatment with the second injection of 2 grams. One patient with herpes zoster (shingles) and encephalitis symptoms benefited in that the severe headache of several days' duration was eliminated in the first 22 hours and stiffness of the neck gradually disappeared while fever and toxicity regressed within 24 hours.

Various changes and modifications can be made in the present invention without departing from the spirit and scope thereof. The various embodiments which have been disclosed herein were for the purpose of further illustrating the invention but were not intended to limit it.

I claim:

1. A method of treating herpes simplex which comprises the administration of an anti-herpetic effective amount of spectinomycin or a non-toxic salt thereof to an individual in need of such treatment.

2. The method of claim 1, wherein the spectinomycin is administered intramuscularly.

3. The method of claim 2, wherein the spectinomycin is employed as the dihydrochloride pentahydrate salt thereof.

4. The method of claim 3, wherein the spectinomycin is administered in combination with an inert diluent.

5. The method of claim 4, wherein the diluent is bacteriostatic water containing benzyl alcohol.

6. The method of claim 5, wherein the amount administered is at least about 4 grams.

7. The method of claim 5, wherein the amount administered is about 4 grams.

* * * * *